US006191341B1

(12) United States Patent
Shippert

(10) Patent No.: US 6,191,341 B1
(45) Date of Patent: Feb. 20, 2001

(54) MEDICAL ABSORBENT PACK SUBSTANTIALLY FREE OF UNWANTED ADHESION PROPERTIES

(76) Inventor: Ronald D. Shippert, 4975 S. Albion St., Littleton, CO (US) 80121

( * ) Notice: Under 35 U.S.C. 154(b), the term of this patent shall be extended for 0 days.

(21) Appl. No.: 09/063,642

(22) Filed: Apr. 21, 1998

(51) Int. Cl.⁷ ............................. A61F 13/15; A61F 13/00
(52) U.S. Cl. ..................... 604/383; 604/304; 604/904; 604/385.18; 602/47
(58) Field of Search ................... 604/363, 904, 604/11–18, 383, 378, 1–3, 304; 602/41–43, 47

(56) References Cited

U.S. PATENT DOCUMENTS

| | | | |
|---|---|---|---|
| 810,127 | * | 1/1906 | Green .................................... 604/378 |
| 2,328,795 | * | 9/1943 | Finks .................................... 604/904 |
| 2,877,765 | * | 3/1959 | Bunyan ................................. 602/41 |
| 3,340,874 | * | 9/1967 | Burgeni ................................. 604/15 |
| 4,185,626 | * | 1/1980 | Jones et al. ........................... 128/256 |
| 4,226,232 | | 10/1980 | Spence . |
| 4,543,098 | * | 9/1985 | Wolfe et al. .......................... 604/904 |
| 4,664,662 | | 5/1987 | Webster ................................ 604/369 |
| 4,775,377 | | 10/1988 | Sweere . |
| 5,112,325 | * | 5/1992 | Zachry .................................. 604/384 |
| 5,147,338 | | 9/1992 | Lang et al. . |
| 5,350,371 | | 9/1994 | Van Iten . |
| 5,374,261 | | 12/1994 | Yoon .................................. 604/385.1 |
| 5,403,300 | * | 4/1995 | Howarth ............................... 604/904 |
| 5,466,231 | | 11/1995 | Cercone et al. ...................... 604/369 |
| 5,584,827 | | 12/1996 | Korteweg et al. . |
| 5,632,731 | * | 5/1997 | Patel ..................................... 602/47 |
| 5,667,864 | * | 9/1997 | Landoll ................................ 604/383 |
| 5,713,855 | | 2/1998 | Shippert . |
| 5,928,184 | * | 7/1999 | Etheredge et al. .................... 604/15 |

* cited by examiner

Primary Examiner—Dennis Ruhl
(74) Attorney, Agent, or Firm—Sheridan Ross P.C.

(57) ABSTRACT

An absorbent pack for absorbing body fluids is provided. The absorbent pack includes an absorbent member and an enclosure assembly that surrounds the absorbent member. Apertures are formed in the enclosure member to permit body fluid to pass therethrough and be absorbed by the absorbent member. The enclosure assembly is made of a material that avoids unwanted adherence between the absorbent pack and a patient's skin or other body tissue. The enclosure assembly has a size to allow the absorbent member to expand without being impeded when it absorbs body fluid. A retention member can be joined to an anterior end of the absorbent member to assist in the removal of the absorbent pack from a body cavity. A cap member can be joined to the anterior end in order to avoid the possibility of separation of the anterior end from remaining portions of the absorbent member when the absorbent pack is removed from a body cavity. A radiopaque marker can also be utilized as part of the absorbent pack in any case where it is necessary to locate the absorbent pack using an x-ray image. In another embodiment, the absorbent pack includes two enclosure members that surround the absorbent member. Because portions of the inner enclosure member underlie or cover the apertures of the outer enclosure member, none of the absorbent member is in contact with the patient's tissue when this absorbent pack is used.

16 Claims, 9 Drawing Sheets

FIG. 12
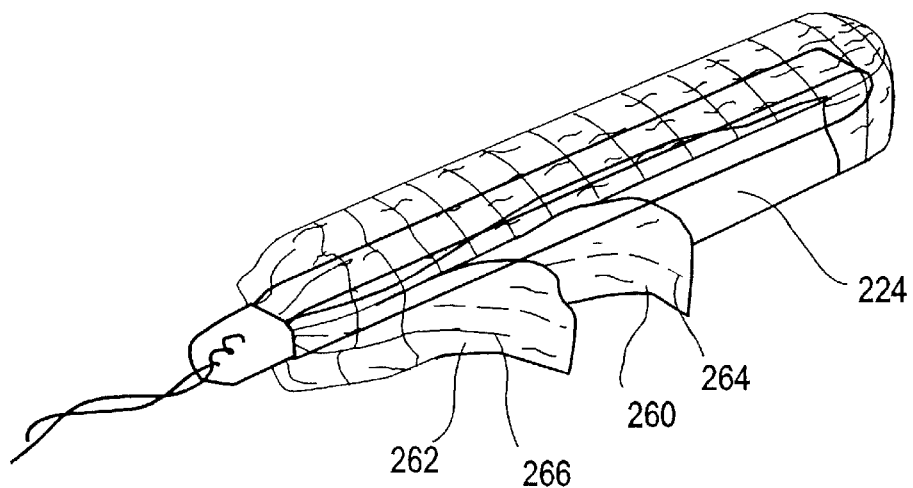
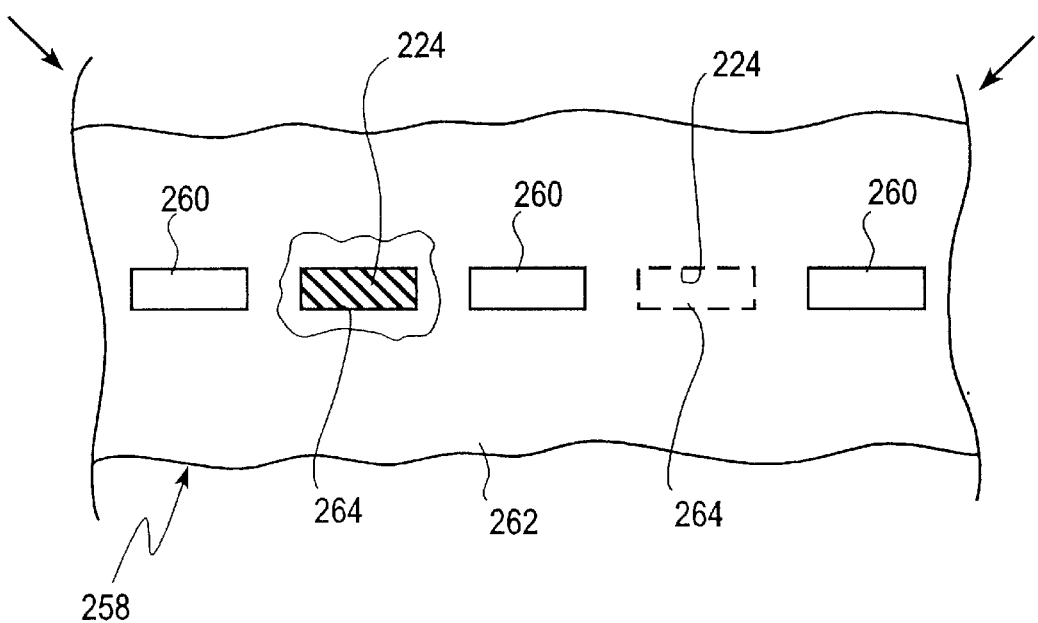
FIG. 13

MEDICAL ABSORBENT PACK SUBSTANTIALLY FREE OF UNWANTED ADHESION PROPERTIES

FIELD OF THE INVENTION

The present invention relates to medical devices including body cavity packs and wound dressings for absorbing body fluids.

BACKGROUND OF THE INVENTION

Numerous absorbent devices have been devised for a variety of applications in the medical field. Their chief objective involves the control of body fluids, particularly by absorbing such fluids. Some absorbent devices are designed to also apply pressure to body tissue in order to control the flow of body fluids, such as blood. These absorbent devices are highly beneficial, for example, after or during surgical procedures, as well as in treating a body wound.

An important function to consider when using such absorbent devices is their tendency to adhere to the body area at which they are placed, if they remain at that position for any length of time. The healing of the tissue or other tissue change, together with the absorbent device drying out, results in the absorbent device becoming attached to the body's skin or tissue. When it is time to remove the device from the patient, pain, significant discomfort, or bleeding can be experienced by the patient due to the removal of the device from a sensitive or tender body area.

The adherence between the absorbent device and the body area is typically caused by the material of the absorbent device that contacts the patient's skin or other tissue. In order to alleviate this adherence, it is known to utilize a non-absorbent material or layer outwardly of the absorbent material. This layer prevents adherence of the absorbent device to the patient's body area. To permit access to the absorbent material, it is necessary that some holes be formed through the non-adhering layer to the absorbent material beneath the non-adhering layer. In one device that uses such a non-adhering layer, at least one side, preferably the longitudinal side, of the absorbent material is laminated with a non-adhering layer. However, not all outer surfaces are laminated.

Notwithstanding the variety of medical absorbent devices that have been advanced for absorbing body fluids, it would be beneficial to provide such a device that further enhances the non-adhering feature associated with absorbent packs. In that regard, it would be advantageous to provide an absorbent pack that further reduces or eliminates any contact between the body area and the absorbent material itself.

SUMMARY OF THE INVENTION

In accordance with the present invention, a medical device or absorbent pack is provided for controlling the flow of body fluids including blood flow from body cavities, wounds and other breaches in the patient's body. In one embodiment, the absorbent pack is a body cavity pack that is used to absorb body fluids, such as blood, that might be present in the nasal, sinus or ear cavities. In another embodiment, the absorbent pack constitutes a wound dressing that can be applied, for example, to the outer skin of a patient in order to absorb or prevent flow of body fluids.

The body cavity pack includes an absorbent member that absorbs the blood or other body fluid. The absorbent member is usually elongated and has six surfaces or sections including upper and lower sections, interior and posterior ends and first and second elongated sides. In one embodiment, the absorbent member has two states related to its use as a body fluid absorbent. In its first or unexpanded state, the absorbent member is compressed or in a normal, uncompressed state. When compressed, the degree of compression is sufficient to enable the absorbent member to be comfortably and conveniently placed in the desired body cavity where it will be used to absorb body fluid. The second or expanded state of the absorbent member refers to its state or condition after it has performed its function of controlling body fluid flow by, for example, absorbing such body fluid. The size or volume of the absorbent member in its expanded state is greater than in its unexpanded state. In this embodiment, this size or volume difference depends on the particular body cavity and the size of the user or patient, i.e. whether the user is an adult or a child. Relatedly, the change to the expanded state commonly involves expansion of the width and height or thickness, and not the length because it is usually not compressed, of the absorbent member.

In another embodiment, the absorbent member is, not only not compressed, but also essentially does not expand in size when it absorbs fluid. Such an absorbent member can be made from a material that has cells or pores, for example, that enable it to absorb body fluids without expansion in size.

With respect to avoiding unwanted adherence between the absorbent member and the walls of the body cavity, an enclosure assembly completely surrounds the absorbent member. The enclosure assembly is made of a material, particularly the outer surface thereof, which has non-adhesion properties whereby such outer surface portions do not, or insubstantially, adhere to the body cavity walls. The enclosure assembly has a number of apertures through which the body fluid can pass to be absorbed by the absorbent member. Accordingly, at most, there are relatively small areas of contact between the body cavity walls and the absorbent member, particularly where the absorbent member portions are exposed through the apertures of the enclosure assembly. Preferably, when the absorbent member is compressed, the size or volume of the expanded state of the absorbent member is at least two times the size or volume of the unexpanded state thereof.

In one embodiment, the enclosure assembly includes a single enclosure member or bag. This enclosure member is also defined as having an anterior end and a posterior end. The anterior end of the enclosure member is adjacent to the anterior end of the absorbent member and the posterior end of the enclosure member is adjacent to the posterior end of the absorbent member. When the body cavity pack is located in a body cavity, the posterior ends are relatively farther away from the exit or opening associated with the body cavity, while the anterior ends are located relatively closer to the opening or exit associated with the body cavity. The enclosure member containing the absorbent member in its unexpanded state is placed in the desired body cavity. The absorbent member absorbs the body fluid that it receives through the apertures in the enclosure member. After the absorbent member absorbs the body fluid, it is usually advantageous for the absorbent member to expand to a size or volume that causes the enclosure member to contact the body cavity walls and exert a pressure there against. Such pressure application is beneficial, for example, in controlling blood flow in nasal or sinus cavities of a patient's nose. In accordance with this application, all or substantially all outer portions of the enclosure member contact the patient's body cavity, while relatively minor parts of the absorbent member through the apertures in the enclosure member are in contact with the body cavity walls.

With regard to removal of the absorbent member and the enclosure member from the body cavity, a retention or string member is preferably joined to at least one of the anterior ends of the absorbent member and the enclosure member. The opposite end of the attachment member can be taped or otherwise held to a convenient or satisfactory part of the patient's body, such as the patient's face when the body cavity is a nasal or sinus cavity. When it is appropriate to remove the absorbent member and the enclosure member of the body cavity pack, the attachment member is pulled to draw them from the body cavity, while no adherence, or substantially none, occurs between the enclosure member and the body cavity walls.

In one embodiment, a cap member is disposed about the anterior ends of the enclosure member and the absorbent member. In that regard, the anterior end portions of the enclosure member are wrapped or otherwise positioned about the anterior end of the absorbent member and the cap member is placed over these two anterior end portions. In this embodiment, the end of the retention member is placed through the cap member, as well as such anterior end portions of both the absorbent member and the enclosure member. The cap member is useful in preventing any possible severing or breaking away of the anterior end portions when the absorbent pack is removed from the body cavity, such as might occur when the retention member is pulled on and could possibly cause the anterior end portions to be separated from the remaining portions of the absorbent member. With respect to the physical characteristics of the enclosure member, it preferably does not expand in size. And, it does not expand in size like the absorbent member when the absorbent member is first compressed and then later absorbs body fluid. In such a case, the enclosure member is greater in size than the absorbent member in its state before absorption of body fluid to allow expansion thereof to its expanded state. More particularly, the enclosure member has inner dimensions or size that are at least equal to the outer dimensions or size of the absorbent member when it is in its expanded state or after it has completed its absorption of the body fluid.

In a preferred embodiment, a radiopaque element is provided with the body cavity pack for the purpose of being able to ascertain the location thereof, in the unlikely event that the absorbent pack unwantedly passed into the interior of the patient's body, such as being aspirated by the patient or user from a nasal cavity. An x-ray procedure can be utilized to find the absorbent member and the enclosure member within the patient's body using the x-rays that interact with the radiopaque element so it is visible on the x-ray image. The radiopaque element can take one or more of a variety of forms, such as being included with the absorbent member, the enclosure member and/or the retention member.

In a further embodiment, the enclosure assembly has two enclosure members or bags. A first enclosure member surrounds the absorbent member and the second enclosure member surrounds the first enclosure member. Each of the two enclosure members has a plurality of apertures. The apertures of the second enclosure member are offset from the apertures of the first enclosure member. When this absorbent pack is assembled, portions of the first enclosure member underlie and inwardly cover the apertures of the second enclosure member. When being used to absorb body fluid, the body fluid first passes through the apertures of the second enclosure member. The body fluid then contacts at least portions of the first enclosure member that underlie these second enclosure member apertures and moves to the apertures of the first enclosure member. The body fluid then passes through these apertures and is absorbed by the absorbent member. In this embodiment, none or virtually none of the absorbent member is in contact with the patient or user of the absorbent pack. Instead, the patient's skin or other tissue is contacted only or substantially only by major portions of the outer surface of the second enclosure member and minor portions of the outer surface of the first enclosure member (i.e. those portions that underlie the apertures in the second enclosure member).

Based on the foregoing summary, a number of salient aspects of the present invention are readily understood. A medical device or absorbent pack for absorbing body fluids is provided that avoids unwanted adherence between the pack and the patient's body area. Consequently, patient discomfort or pain is substantially reduced or eliminated when the pack is removed from the patient's tissue. The absorbent pack can be used in a variety of applications including as a body cavity pack in the nose or ear, as well as a wound dressing. In one embodiment, the absorbent member is able to expand and apply pressure to body cavity walls through the enclosure assembly. The enclosure assembly does not impede expansion of the absorbent member due to its physical characteristics in which it is preferably greater in size than the absorbent member before it absorbs body fluid. The enclosure assembly can include a double enclosure member or bag configuration in which apertures are offset so that no contact at all between the absorbent member and the patient is achieved. A cap member can also be employed to reduce the risk that a retention member will be separated from the absorbent member and/or enclosure member when the absorbent pack is removed from a body cavity. The absorbent pack can also include a radiopaque material to enable it to be easily located using an x-ray image.

Additional advantages of the present invention will become readily apparent from the following discussion, particularly when taken together with the accompanying drawings.

BRIEF DESCRIPTION OF THE DRAWINGS

FIG. 12 illustrates a perspective view of the absorbent pack of the embodiment of FIG. 10 that shows portions of each of the first and second enclosure members being cut away;

FIG. 13 illustrates an enlarged, cut-away section of the absorbent pack of FIG. 9 and a further cut-away illustrating the apertures of the two enclosure members;

DETAILED DESCRIPTION OF THE PREFERRED EMBODIMENT

Figure 1:
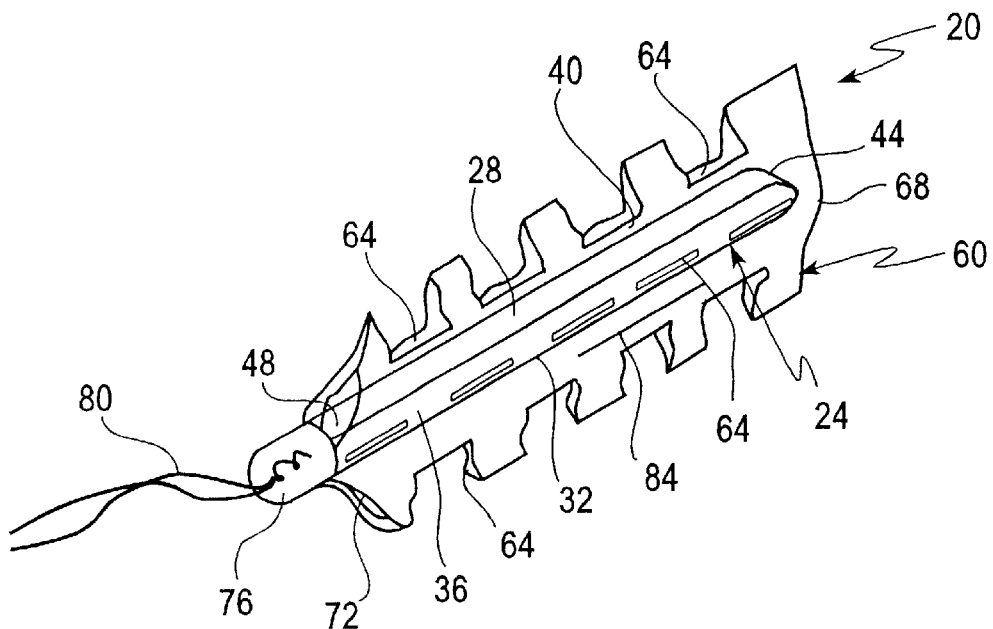
FIG. 1 illustrates a perspective view of an absorbent pack in an unexpanded state and with a single enclosure member.

With reference to FIG. 1, a medical device or absorbent pack 20 for absorbing body fluids is illustrated. The absorbent pack 20 can be used with or applied to a number of body areas for absorbing body fluids, such as blood. In the embodiment of FIG. 1, the absorbent pack 20 has particular utility in absorbing blood present in body cavities, such as in the nose or ear to prevent or otherwise control blood flow in these body cavities.

The absorbent pack 20 includes an absorbent member or pad 24 that is generally elongated in shape and has the following sections or outer surfaces: an upper section 28, a lower section 32, a first or right longitudinally extending side 36 and a second or left longitudinally extending side 40, a posterior end 44 to be located farther or more deeply into the body cavity and an anterior end 48 that is to be located relatively more adjacent to the exit or open end of the body cavity than is the posterior end 44.

In one embodiment, the absorbent member 24 is made from polyvinyl acetal (PVA), which is a well-known and widely utilized material for absorbing liquids including blood. As seen in FIG. 1, the absorbent member 24 has been compressed so that it is in an unexpanded state whereby it has not received or absorbed any liquid. In achieving the compressed or unexpanded state of the absorbent member 24, in one embodiment, the absorbent member 24 is formed so that there is a relative delaying or slowing of body liquid absorption by the absorbent member 24. Such controlled absorption is realized during the compression steps or stages in forming the absorbent member. That is, the absorbent member 24 has a number of minute cells or pores that are involved with the liquid absorption. When compressing the absorbent member 24 to create the unexpanded state, the pressing or compression mechanism is controlled to move or press the absorbent member 24 relatively slowly such that the number and/or size of such cells are not destroyed, but regulated to achieve a resulting configuration by which, when the absorbent member 24 is utilized to absorb a liquid, it does so in a relatively delayed manner; in contrast to an absorbent member 24 that is formed by using a substantially greater speed of pressing or compression. Depending on other factors including the desired application for the absorbent member 24, it can be compressed in more than one plane to achieve a desired unexpanded volume or size. Typically, the unexpanded state of the absorbent member is such that, upon contact or receipt of a body fluid, it expands along its width and height or thickness, but not in a direction along its length or longitudinal extent.

The absorbent pack 20 also includes an enclosure member or sack 60 that preferably completely encloses or surrounds the absorbent member 24. More specifically, the enclosure member 60 has portions that surround each of the upper and lower sections 28, 32, first and second sides 36, 40 and posterior and anterior ends 44, 48 of the absorbent member 24. The enclosure member 60 is made from a material that, at least at its outer surface, avoids adherence to the body area with which it is used or applied. The greater the smoothness of the surface of the enclosure member 60, the less it tends to adhere to the body area by drying and/or in-growth. In one embodiment, the enclosure member or sack 60 is made of a polymeric material that is hydrophobic and is in the range of 0.0005–0.003 mm in thickness. It is known to laminate the outer surface of an absorbent pad in order to provide smoother surfaces on two sides on the absorbent pad. However, such an absorbent pad is still prone to sticking to the body area with which it is used because the other four surfaces are exposed to tissue and/or air. From a practical viewpoint, it is only feasible to laminate on two surfaces because the lamination interferes with the compression process. Consequently, difficulty remains in removing such an absorbent pad from a body cavity due to non-laminated portions of the absorbent pad adhering to body tissue. The enclosure member 60, on the other hand, surrounds all six outer surfaces of the absorbent member 24 to alleviate the occurrence of such unwanted adhesion.

In order to permit the absorbent member 24 to receive and absorb body fluid through the enclosure member 60, apertures 64 are formed through the thickness of the enclosure member 60. The enclosure member 60 is generally made of a liquid impervious material, which does not permit blood or any other body liquid to pass through it. Hence, a number of apertures 64, preferably formed in a pattern throughout the enclosure member 60 are provided to permit the passage of body fluid therethrough for absorption by the absorbent member 24. Generally, the enclosure member 60 has portions that are cut out in selected areas and sizes to allow for body fluid to enter and be absorbed by the absorbent member 24, while allowing a minimum or reduced in-growth of the absorbent member 24 into body tissue. The apertures 64 can be in the form of elongated openings or slits, with such slits having a dimension along their lengths in the range of 10–200 mm. The total area of such apertures 64 relative to non-aperture portions of the enclosure member is in the range of 19–31%. Stated another way, the total areas of all the apertures 64 is at least 19% of the total surface area of the enclosure member 60.

With respect to the normal size and volume of the enclosure member 60, it is preferably greater than the size and volume of the absorbent member 24. When the absorbent member 24 absorbs body fluid and expands in size, the enclosure member 60 does not impede such expansion; rather, the size of the enclosure member 60 enables the absorbent member 24 to expand within the confines of the enclosure member 60. This loosely-fitting enclosure member 60 results in a further advantage related to creating effectively greater aperture size when a body fluid, such as blood, is present adjacent to the absorbent pack 20. This discussion will be continued in the context of an example in which apertures 64 are in the form of slits that have a 1.25×10 mm dimension. With this example, since the enclosure member 60 is loosely provided about the absorbent member 24, and not stretched tightly thereabout, the 1.25×10 mm rectangular aperture will be made more elliptical or circular by the body liquid forcing its way through the aperture. Upon exposure to blood, for example, the blood would move toward the dry parts of the absorbent member 24 through the rectangular-shaped aperture 64. During this process, the aperture size will be determined by the amount of blood flowing from wet portions to dry portions. The amount of blood that flows will be determined as a function of the amount of blood present on the wet side and any additional pressure from the blood, such as due to arterial blood pressure, together with the "pull" or drawing in of the blood by the dryer absorbent member portions as the cells thereof fill up with blood and expand. Based on this, it is logical to conclude that at times the apertures 64 will remain at the 1.25 mm×10 mm size and at times that such apertures will expand in size and occasionally open up to a maximum size. In the context of the foregoing example, a rectangular surface area of 1.25 mm×10 mm is effectively changed into an elliptical shape and then a circular shape. The rectangular surface area of 1.25 mm×10 mm equals 22.5 mm. When the rectangular surface area changes to a circular surface area due to the foregoing factors when a liquid, such as blood, is present, the surface area becomes 40 sq. mm. This determination is based on the calculation of π×radius². The radius is determined as being one-half of the diameter. The diameter is determined by dividing the rectangular surface area of 22.5 mm by π.

Returning to a discussion of the enclosure member 60, it has a posterior end 68, which is adjacent to the posterior end 44 of the absorbent member 24. The enclosure member 60 also has an anterior end 72 that is adjacent to the anterior end 48 of the absorbent member 24. In the illustrated embodiment of FIG. 1, the posterior end 68 of the enclosure member 60 is spaced and detached from the anterior end 44 of the absorbent member 24. However, the anterior end 72 is wrapped or positioned about the anterior end 48 of the absorbent member 24. This is beneficial in this embodiment that utilizes a cap member 76 that is disposed about at least the anterior end 48 of the absorbent member 24 and preferably also disposed about the anterior end 72 of the enclosure member 60. In accordance with this embodiment, a retention or string member 80 is stitched or otherwise positioned through the cap member 76, as well as the anterior ends 48,72 of the absorbent member 74 and the enclosure member 60, respectively. The retention member 80 is particularly useful in preventing unwanted swallowing or aspirating of the absorbent pack 20, namely, the absorbent member 24 and the enclosure member 60 by the patient when the absorbent pack 20 is used in a body cavity, such as a cavity in the nose. More specifically, the retention member 80 is attached to a body portion of the patient or user at a sufficient distance from the body cavity, such as being attached to the face when the absorbent pack is positioned in a cavity in the nose. Such attachment ensures that the absorbent pack 20 will not be aspirated into the patient.

The retention member 80 is also used in removing or pulling the absorbent pack 20 from the body cavity. In the absence of such a cap member 76, the pulling using the retention member 80 could possibly cause a complete tearing away or severing of the anterior end portions of the absorbent member 24 from remaining portions thereof. If that should occur, problems arise in attempting to remove such remaining portions from the body cavity. The strength and rigidity of the cap member 76 avoids the occurrence of any such severing of portions due to the removal of the absorbent pack 20. The cap member 76 can be made from a variety of materials, which may be pre-formed, molded or dipped. Such materials can include polyethylene, silicone, polytetrafluorethylene, polypropylene, ABS, nylon, acetyl, polycarbonate and polyesters. Optionally, such a cap member 76 may not be utilized. Instead, for example, the retention member 80 might be fastened or stitched to the enclosure member 60 and not to the absorbent member 24. In either case, it is preferred that the anterior end 72 of the enclosure member 60 be narrowed or streamlined at its anterior end 72 in connection with facilitating its positioning and removal relative to a body cavity. Other than the cap member 76, such configurations of the enclosure member 60 at its anterior end 72 to achieve a smooth, air-resistant tip that is not in contact with body tissue could include a drawstring, glue, shrink wrap sewing the anterior end 72 shut and sewing through the enclosure member 60 and the absorbent pack 20.

Diagrammatically represented in FIG. 1 is also a radiopaque element 84. In one embodiment, the radiopaque element 84 is embedded in or otherwise formed with the enclosure member 60. The radiopaque element 84 is x-ray detectable. In the unlikely event that the absorbent pack 20 is aspirated or otherwise moves into the interior of the patient's body, an x-ray image can be used to locate and/or monitor the position of the absorbent pack within the patient. The radiopaque element 84 can be a metal, such as barium sulfate, that is molded into the enclosure member 60. Other materials or substances could be utilized including bismuth triodide. Alternatively or additionally, the radiopaque element 84 could be integrated, incorporated, or otherwise included with the retention member 80 and/or the absorbent member 24.

Figure 2:
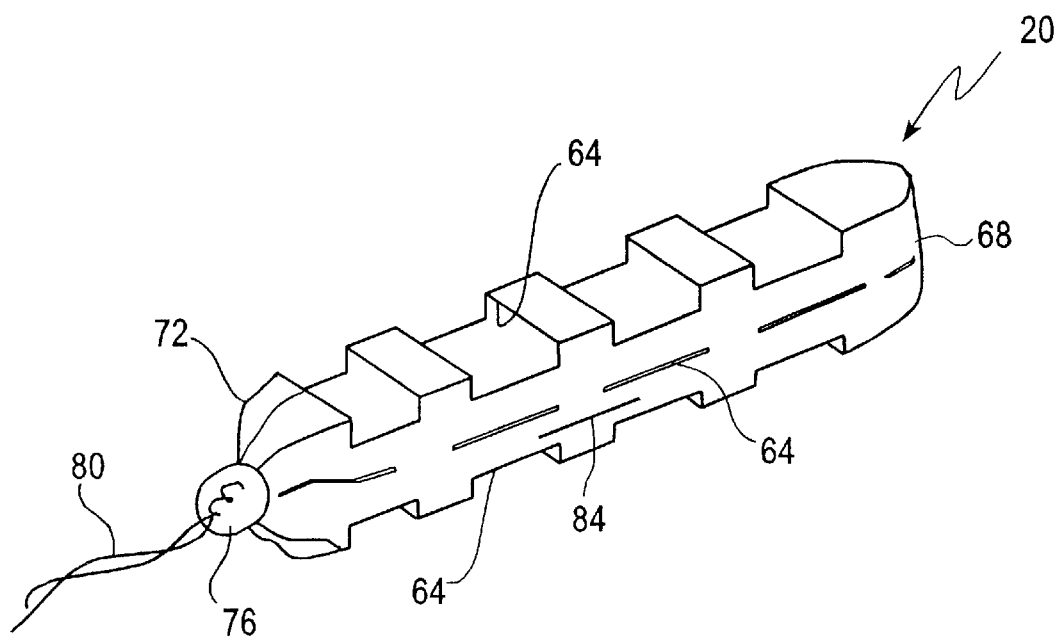
FIG. 2 illustrates a perspective view of the absorbent pack of FIG. 1 but with the absorbent member in its expanded state.

With reference to the FIG. 2 as well, the absorbent member 24, upon absorbing body fluid changes from its unexpanded state of FIG. 1 to its expanded state. A representative fully-expanded state is depicted in FIG. 2. As can be seen, the expanded state of the absorbent member 24 approaches or is almost comparable in size or volume to the enclosure member 60. That is to say, when in its expanded state due to absorption of one or more body fluids, the absorbent member 24 occupies all or substantially all of the inner size and volume of the enclosure member 60 that it had, as shown in FIG. 1, i.e. when the absorbent member 24 is in its unexpanded state. From a quantitative viewpoint, the absorbent member can take a variety of sizes to accommodate different sized body cavities. Different sizes are made available for infants through adults. Furthermore, wide and narrow forms of the absorbent member can be provided. Each of the following sizes refer to an expanded, or substantially expanded, absorbent member 24. In the case of a nasal absorbent pack, the volume of the absorbent member is in the range of 1.0–50 cc and, more preferably, in the range of 1.9–30 cc. For an ear absorbent pack, the volume of the absorbent member 24 is in the range of 0.5–4.5 cc, and more preferably in the range of 1.5–2.5 cc. For a sinus absorbent pack, the volume of the absorbent member is in the range of 1.0–5 cc and, more preferably, in the range of 1.2– 3.84 cc. For a wound dressing or absorbent pack, different sizes of absorbent members can be employed. A small wound dressing has an absorbent member with a volume of about 5 cc. A medium-sized absorbent member used as a wound dressing has a size of about 50 cc. A large-sized absorbent member used as a wound dressing has a size of about 400 cc. Each such absorbent member expands at least twice the volume that it has in its unexpanded state. Preferably, the range of expansion is 2—about 12 times in volume from the unexpanded state to the expanded state. In quantifying the volume, size, or dimensions of the enclosure member 60, particularly its inner dimensions, the inner sizes of the various sizes of the enclosure member 60 are larger than the expanded states of the absorbent members that they surround. They are preferably 1%–20% larger so that such enclosure members 60 will not impede the change of their respective absorbent members 24 when they absorb body fluids and change from the unexpanded state to the expanded state.

Figure 3:
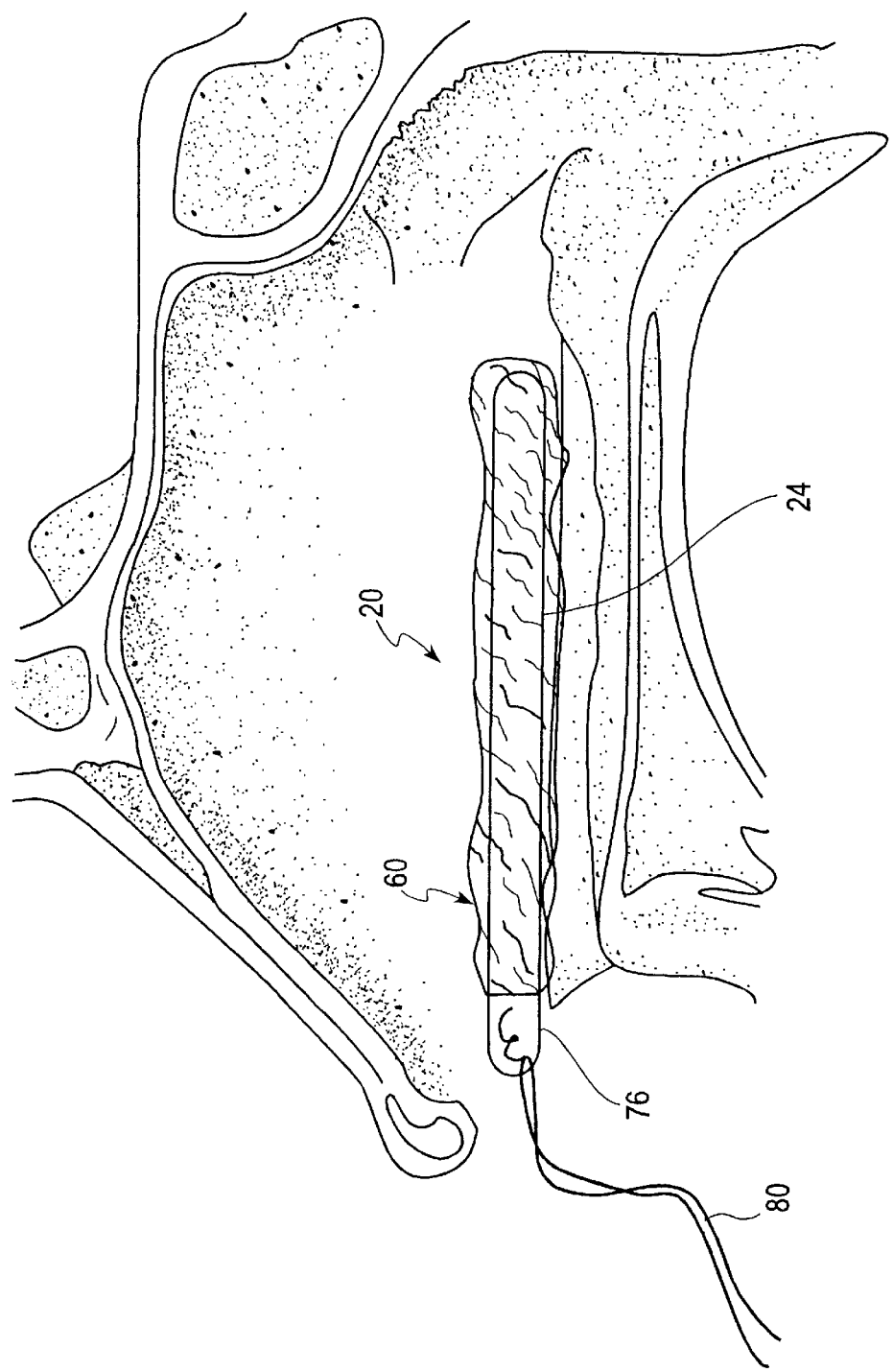
FIG. 3 illustrates the absorbent pack of FIG. 1 in a nasal cavity.
Figure 4:
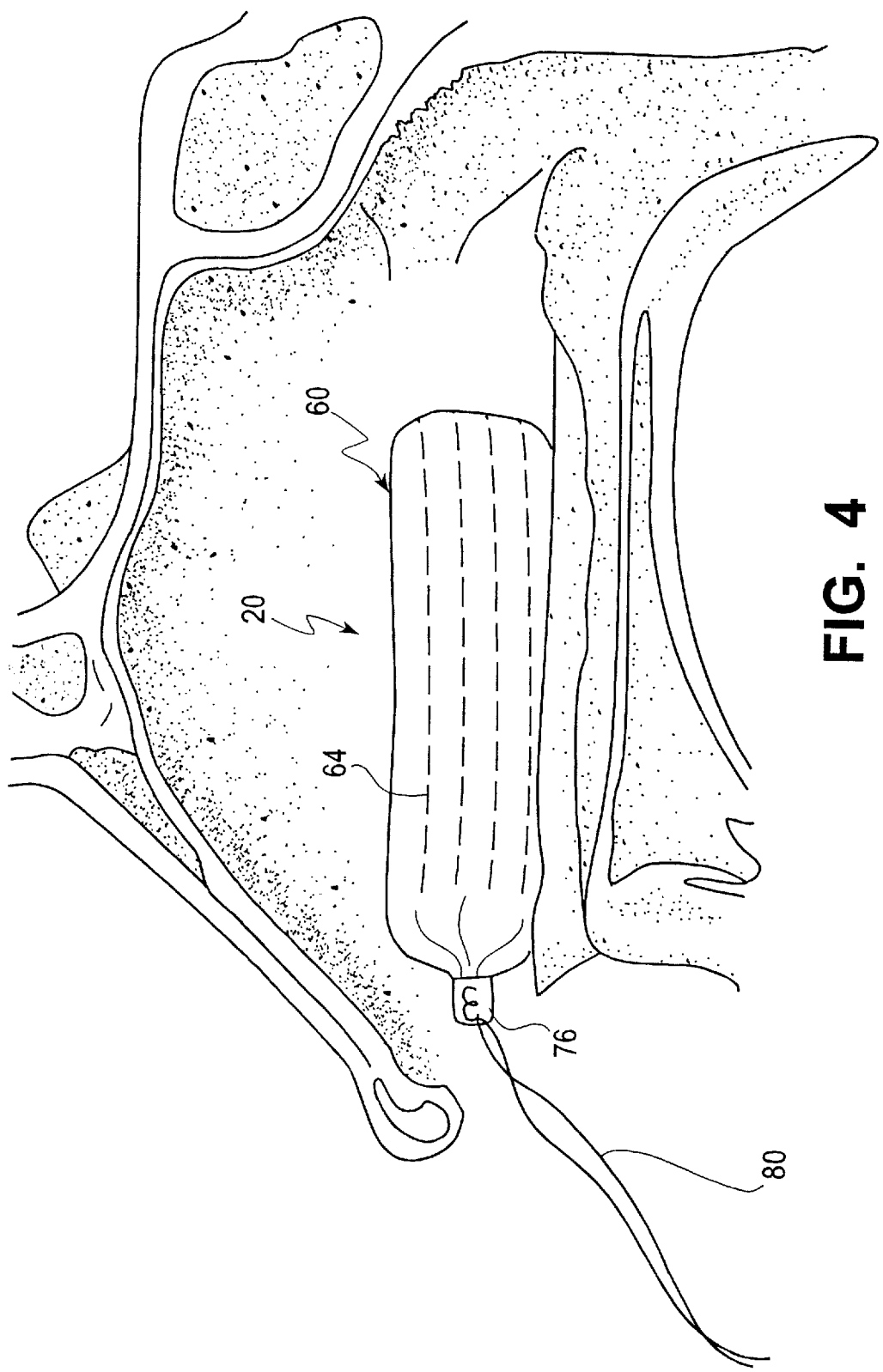
FIG. 4 illustrates the absorbent pack of FIG. 3 with the absorbent member in its expanded state.

With regard to an application of the absorbent pack 20, reference is next made to FIGS. 3 and 4. FIG. 3 illustrates a nasal cavity with an absorbent pack 20 located therein and with the absorbent member 24 being in its unexpanded state. Once located in this nasal cavity, the absorbent pack 20 can control bleeding, for example, and absorb the blood that is present in this cavity thereby reaching the expanded state of FIG. 4. As can be understood from a comparison of FIGS. 3 and 4, the absorbent member 24 has reached its expanded state without being subjected to any impeding or compressing force that might be caused by a more tightly fitting enclosure member 60. With regard to such expansion, as previously noted, the blood is able to pass through the pattern of apertures 64 formed through the enclosure member 60.

Figure 5:
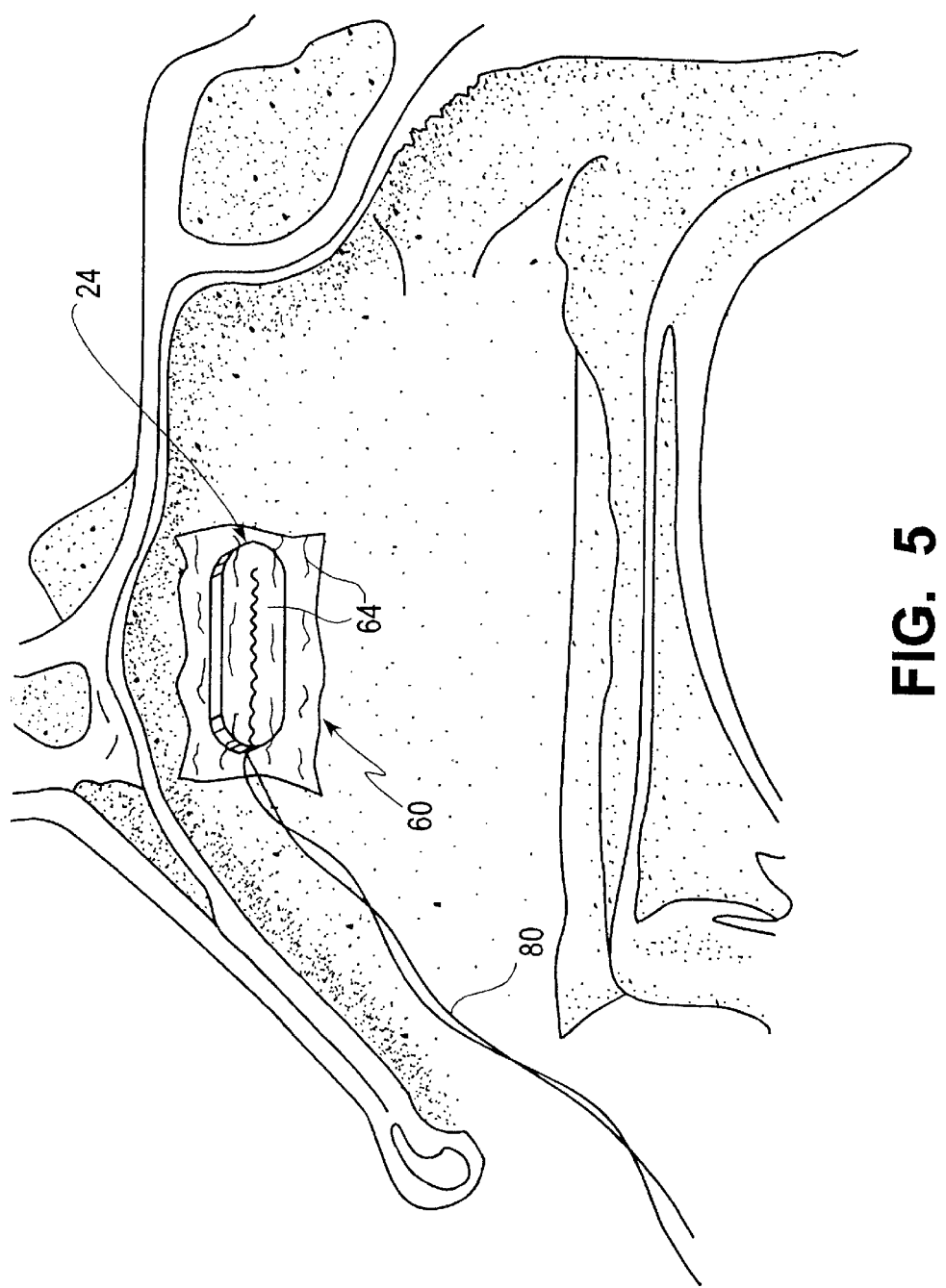
FIG. 5 illustrates an absorbent pack in a sinus cavity.
Figure 6:
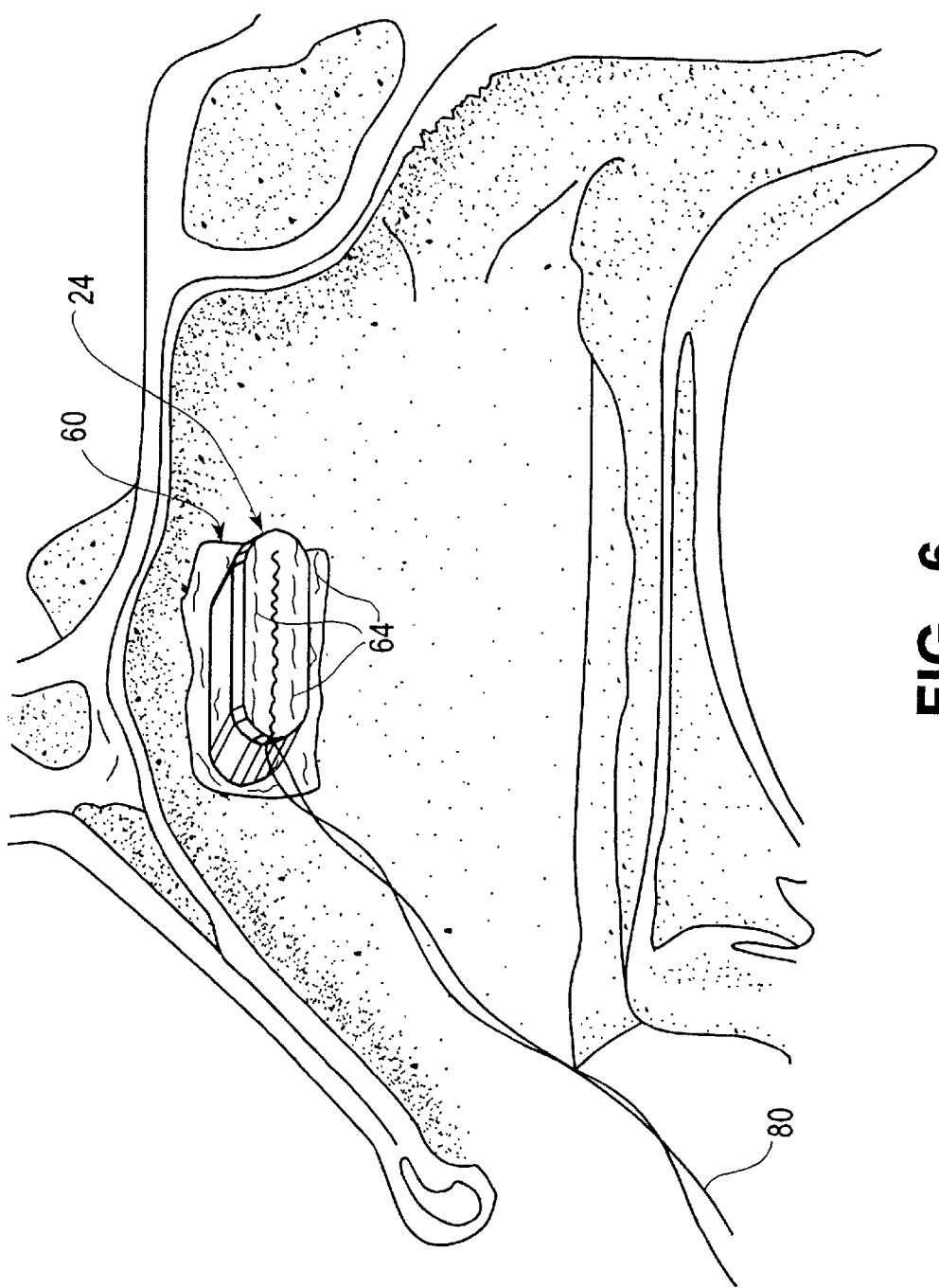
FIG. 6 illustrates the absorbent pack of FIG. 5 with the absorbent member in its expanded state in the sinus cavity.

A further application of such an absorbent pack 20 is conveyed in referring to FIGS. 5 and 6. As seen in FIG. 5, the absorbent pack 20 is located in a sinus cavity of a patient. The enclosure member 60 with the apertures 64 has a greater size or volume to permit the expansion of the absorbent member 24 when it absorbs the blood or other body fluid. The expanded state of the absorbent member 24 is shown in FIG. 6. Like the application of the absorbent member in the nasal cavity of FIG. 4, the absorbent member 24 typically expands to a size that results in applying pressure to the body cavity walls, i.e., the sinus cavity walls. When this occurs, contact is made between the outer surface areas of the enclosure member 60 and the sinus cavity walls. Contact with the walls by the portions of the absorbent member 24, which are exposed through the apertures 64, is reduced and non-problematic.

Figure 7:
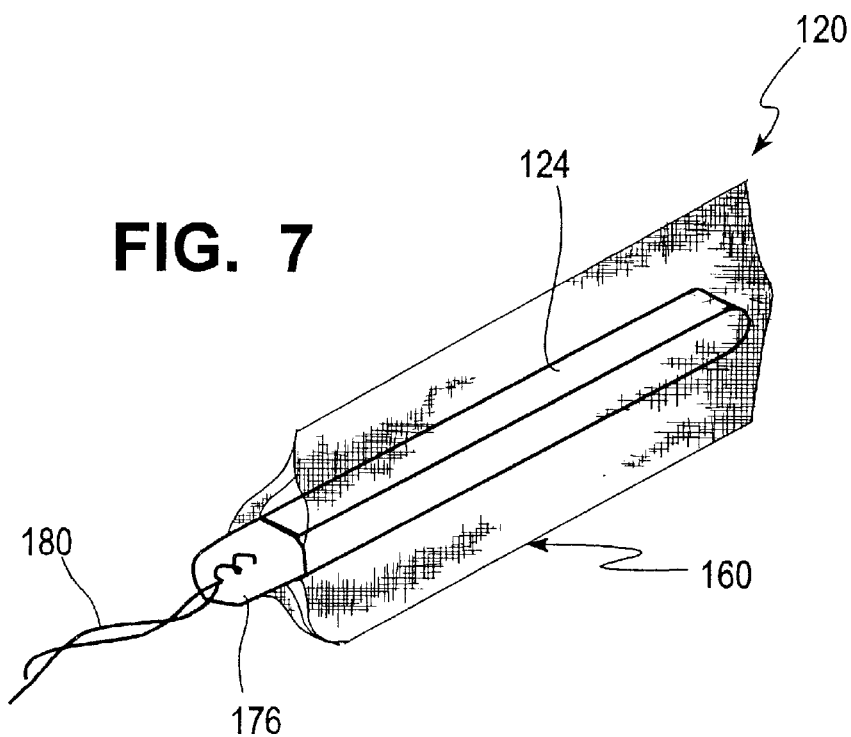
FIG. 7 illustrates a perspective view of another embodiment of an absorbent pack in which the single enclosure member is made from a mesh-type material.
Figure 8:
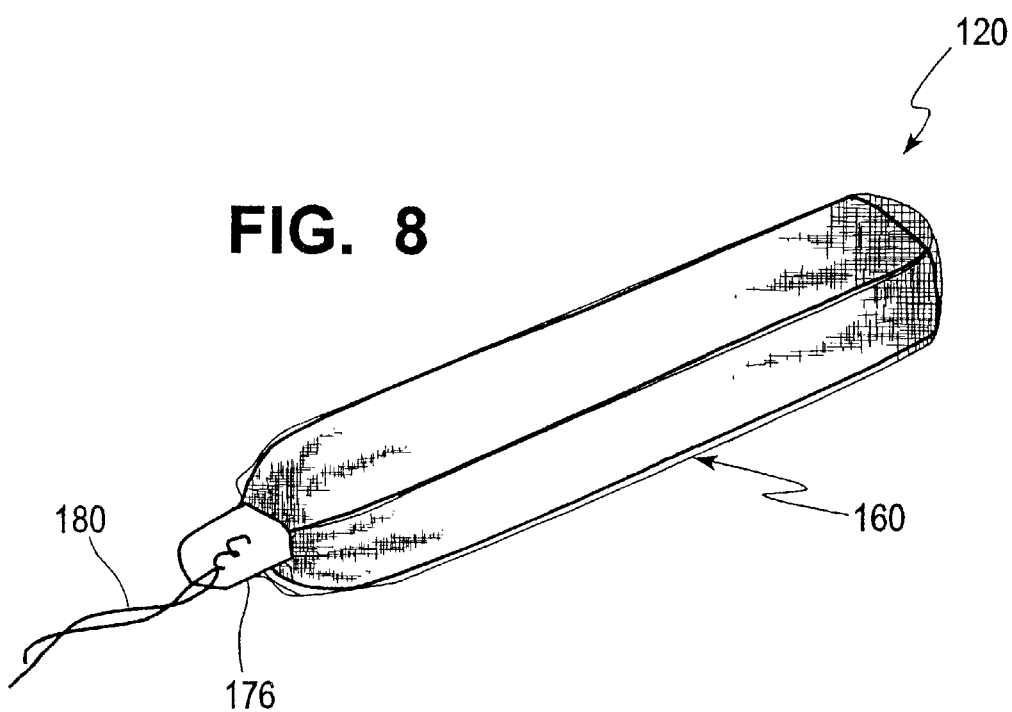
FIG. 8 is a perspective view of the absorbent pack of the embodiment of FIG. 7 and with the absorbent member in its expanded state.
Figure 9:
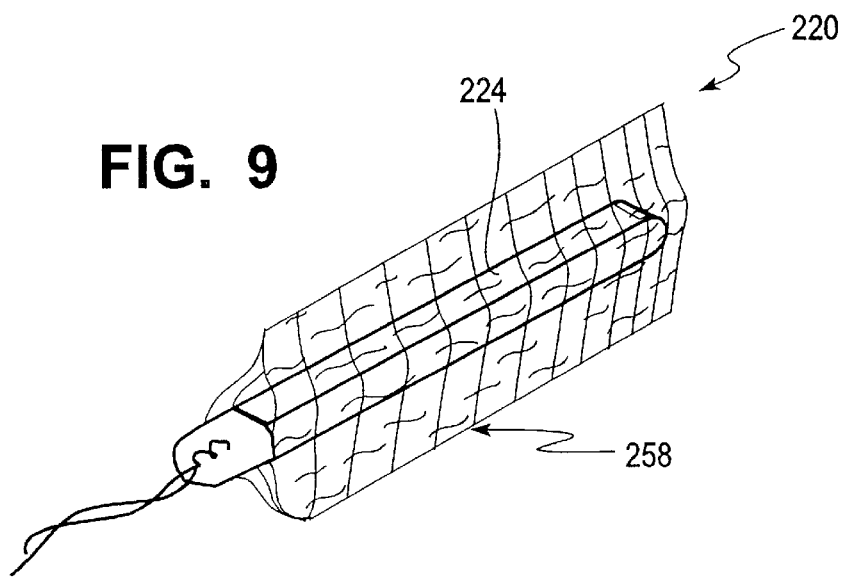
FIG. 9 illustrates a perspective view of an absorbent pack with two enclosure members.

A variant of the embodiment of FIG. 1 is illustrated in FIGS. 7 and 8. In particular, an absorbent pack 120 is illustrated that includes an equivalent or at least comparable absorbent member 124 to that disclosed in FIG. 1. The absorbent member 124 is surrounded by an enclosure member 160, which is functionally equivalent but physically different from the enclosure member 60 of the embodiment of FIG. 1. In particular, the enclosure member 160 is made from a mesh material having minute or very small in size holes through which the body fluid is able to pass to the absorbent member 124. Instead of apertures 64 being cut in an enclosure member 60, as in FIG. 1, the enclosure member 160 is basically made with the minute apertures due to the mesh configuration of this bag or enclosure member. The overall total area of such minute apertures is comparable to the overall total area of the apertures 64 in the embodiment of FIG. 1. Like the embodiment of FIG. 1, the absorbent pack 120 can include a cap member 176 and a retention or string member 180 for the purposes or functions previously described in the discussion of FIG. 1. As represented in FIG. 8, the absorbent member 124 is able to expand when used without being impeded by the enclosure member 160, with the absorbent member 124 expanding due to the body fluid passing through the porous parts or minute apertures in the mesh-style enclosure member 160.

Figure 10:
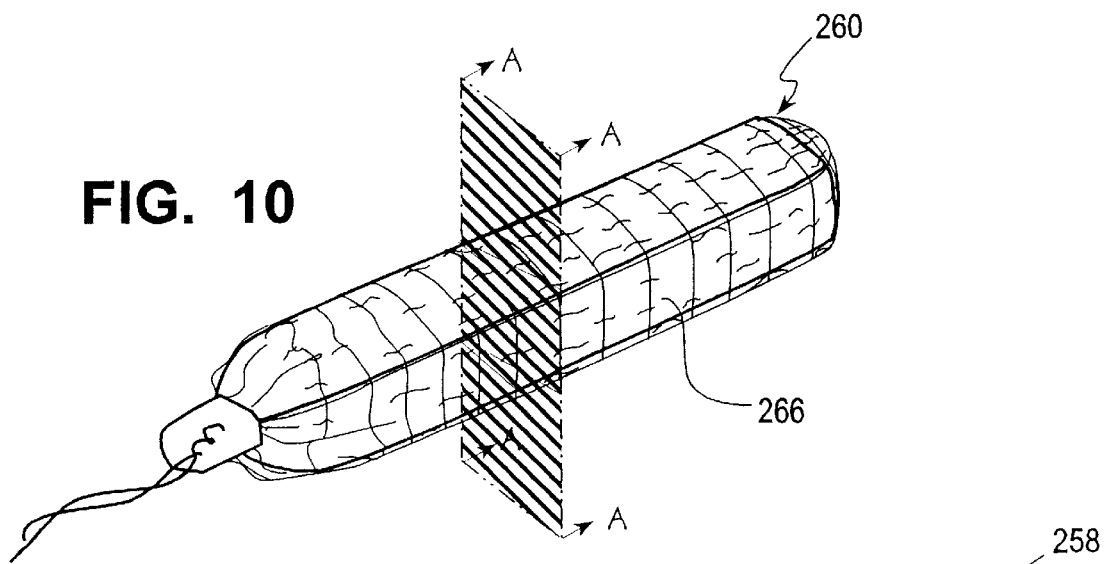
FIG. 10 illustrates a perspective view of the absorbent pack of FIG. 9 with the absorbent member in its expanded state.
Figure 11:
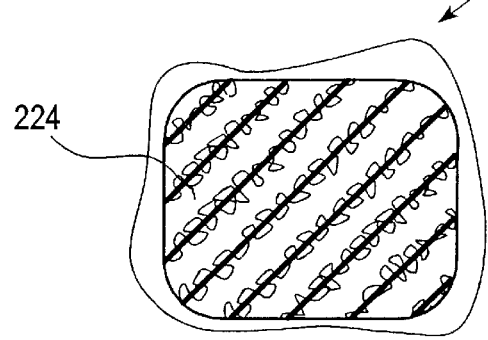
FIG. 11 illustrates a lateral, cross-sectional view of the absorbent pack of FIG. 10 showing the outer surface of the absorbent member having all portions in contact with the enclosure assembly.

With reference to FIGS. 9–13, another embodiment is disclosed for surrounding an absorbent member. More particularly, an absorbent pack 220 is provided that includes an absorbent member 224 that is completely surrounded, as with the other embodiments, but is surrounded by an enclosure assembly 258 that, as seen in FIGS. 12 and 13, includes a first or inner enclosure member and a second or outer enclosure member 262. Accordingly, this embodiment includes two, instead of one, enclosure members or bags that are located about the absorbent member 224. In one embodiment, each of the first and second enclosure members 260,262 is essentially the same as the previously discussed enclosure members 60,160, except that the apertures or minute holes through which the body fluid passes for the two enclosure members 260,262 are not aligned. Specifically, the apertures 264 of the inner enclosure member 260 are offset relative to the apertures 266 of the outer enclosure member 262. Thus, underlying the apertures 266 of the outer enclosure member 262 are solid body portions of the inner enclosure member 260, and not the apertures 264. As illustrated in FIG. 11, the enclosure assembly 258 surrounds the absorbent member 224 in a way that there are no exposed portions of the absorbent member 224. That is to say, the apertures 264 of the inner enclosure member 260 are covered or overlaid with solid body portions of the outer enclosure member 262. In this way, exposed parts of the absorbent member 224 that underlie the apertures 264 of the inner enclosure member 260 are not exposed due to the second, outer enclosure member 262 and the offset apertures 266 thereof. Such a relationship between the apertures 264,266 is further schematically represented in FIG. 13 in which apertures 266 of the outer enclosure member 262 are illustrated as having solid body portions of the inner enclosure member 260 underneath such apertures.

With regard to the expanded state of the absorbent member 224 when it receives and absorbs body fluid, as illustrated in FIG. 10, such is accomplished using both of the apertures 264,266 of the two enclosure members 260,262, respectively. In that regard, the body fluid, such as blood, first enters the apertures 266 of the outer enclosure member 262. Since the inner enclosure member 260 is not in any sealing position or relationship to the outer enclosure member, 262, the blood is able to move or seep past the apertures 266 and contact the underlying, solid body portions of the inner enclosure member 260. The blood is able to continue movement to one or more apertures 264 in the inner enclosure member, where the blood will then pass through those apertures 264 to be absorbed by the absorbent member 224. Accordingly, the body fluid does not take a direct path to the absorbent member 224 but rather traverses a relatively serpentine path as it begins entry through the apertures 266 of the outer enclosure member 262, due to the offset configuration of the two sets of apertures 266,264.

Figure 14:
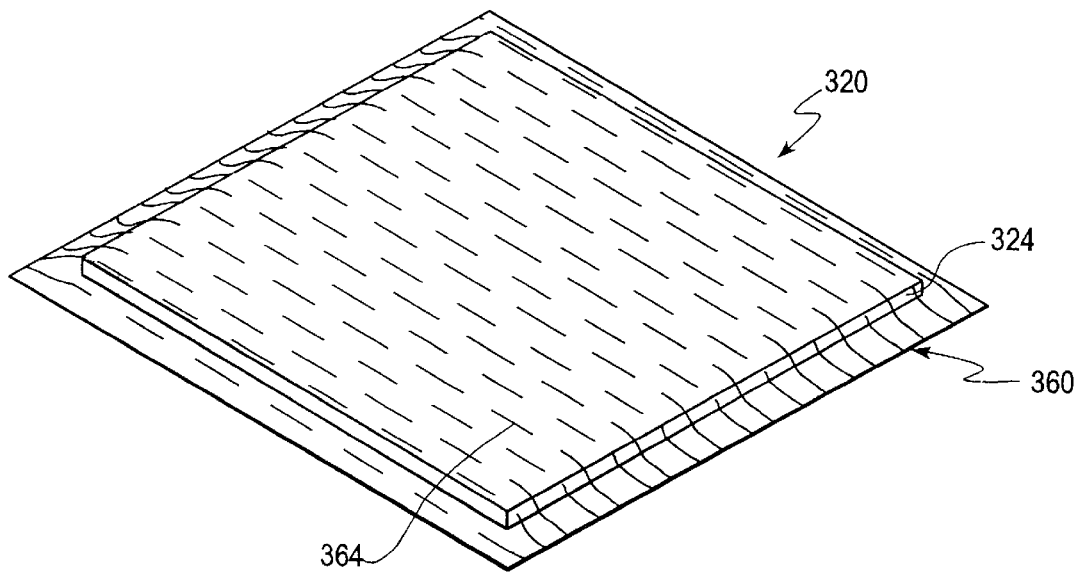
FIG. 14 is a perspective view of another embodiment of the absorbent pack that has particular utility as a wound dressing.
Figure 15:
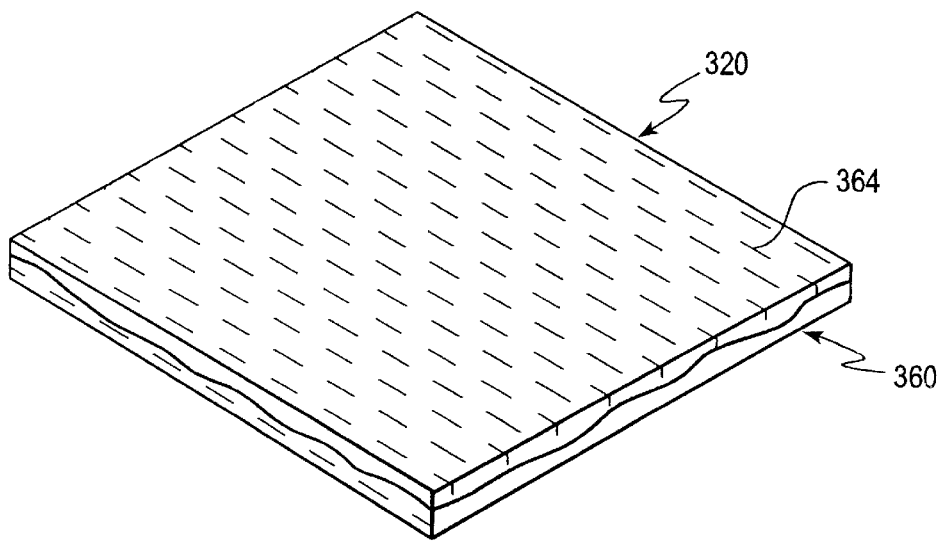
FIG. 15 illustrates a perspective view of the embodiment of FIG. 14 with the absorbent member in its expanded state.

A further application for the absorbent pack of the present invention is illustrated in FIGS. 14 and 15. An absorbent pack 320 is illustrated that has particular utility as a wound pack or dressing. The wound absorbent pack 320 can be applied, for example, to exterior body wounds or breaches in the user's skin. The wound absorbent pack 320 includes an absorbent member 324 that is relatively more square and less elongated than the previously described absorbent packs. Like the other variations or embodiments, the absorbent member 324 is made from a material that readily absorbs blood or other body fluids and changes from its unexpanded state (FIG. 14) to its expanded state (FIG. 15). An enclosure member 360 completely surrounds all outer surfaces or sections of the absorbent member 324. The enclosure member has a plurality of apertures 364, which are preferably formed in a pattern throughout the surface area of the enclosure member 360. The enclosure member 360 is larger in size than the absorbent member 324 in its unexpanded state. When it expands, the expansion of the absorbent member 324 is not impeded by the inner size or volume of the enclosure member 360. As can be appreciated, the wound absorbent pack could also be provided in a double enclosure member or bag configuration.

Although the various embodiments of the absorbent pack 20 have been described in detail as having a compressed volume or size before absorption of body fluid and an expanded volume or size after absorption of body fluid, other embodiments are also contemplated. In another of such embodiments, the absorbent pack 20 has an unexpanded but also an uncompressed state (unabsorbed state). In this embodiment, the absorbent pack 20 is not compressed and can be made of a material that is not intended to be compressed, such as a hydrogel. The hydrogel material is basically a moisture or fluid-absorbing jelly that is not compressed. When in an absorbed state after it has absorbed a body fluid, there is limited expansion thereof due to the body fluid occupying spaces within the hydrogel. However, such expansion is not to the extent previously described in the other embodiments. In still another embodiment, the absorbent pack 20 is characterized by an unabsorbed state, (before absorbing body fluid,) in which it is not or essentially not compressed and an absorbed state, after receiving and absorbing body fluid, and in which there is no or essentially no change in size or volume of the absorbent pack between its unabsorbed state and its absorbed state. In such an embodiment, the absorbent pack 20 could be made from a material that might include polyurethane, which has cells or pores in the unabsorbed state that receive or take up the body fluid without any increase in size or volume of the absorbent pack from its unabsorbed state.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best modes presently known for practicing the invention and to enable others skilled in the art to utilize the invention in such, and other embodiments, and with the various modifications required by the particular application or uses of the invention. It is intended that the appended claims be construed to include alternative embodiments to the extent permitted by the prior art.

What is claimed is:

1. A body cavity pack for insertion in a body cavity having inner walls, comprising:

an absorbent member having upper and lower sections, an anterior and a posterior end, and first and second sides, said absorbent member having an unexpanded state before absorbing body fluid and an expanded state after absorbing body fluid; and an enclosure assembly having a number of apertures for surrounding each of said upper and lower sections, said anterior and posterior ends, and said first and second sides of said absorbent member;

wherein, when said absorbent member and said enclosure assembly are inserted in the body cavity, said absorbent member is capable of absorbing fluid present in the body cavity to change from said unexpanded state to said expanded state and in which said enclosure assembly, in said expanded state of said absorbent member, has a majority of portions thereof that contact the inner walls of the body cavity; and said unexpanded state of said absorbent member having a first size and said expanded state of said absorbent member having a second size and in which said second size is at least two times greater than said first size, said enclosure assembly having a first inner size when said absorbent member is in said unexpanded state and a second inner size when said absorbent member is in said expanded state and in which said second inner size is less than two times said first inner size.

2. A body cavity pack, as claimed in claim 1, wherein:

said enclosure assembly includes a single enclosure member having said apertures.

3. A body cavity pack, as claimed in claim 1, wherein:

said enclosure assembly includes first and second enclosure members with each having interior portions, each of said first and second enclosure members having some of said apertures and in which said apertures of said first enclosure member are offset from said apertures of said second enclosure member such that all portions of said absorbent member contact said interior portions.

4. A body cavity pack, as claimed in claim 1, wherein:

said first inner size remains substantially the same when said absorbent member changes from said unexpanded state to said expanded state.

5. A body cavity pack, as claimed in claim 1, wherein:

said enclosure assembly includes an anterior end joined to said anterior end of said absorbent member and said enclosure assembly includes a posterior end that is detached from said posterior end of said absorbent member.

6. A body cavity pack, as claimed in claim 1, wherein:

said enclosure assembly includes a cap member for surrounding said anterior end of said absorbent member and the body cavity pack further includes a retention member connected to said cap member and in which said retention member is capable of extending outwardly from the body cavity for attachment adjacent thereto.

7. A body cavity pack, as claimed in claim 1, further including:

means for assisting removal of said absorbent member and said enclosure assembly from the body cavity, said means for assisting removal being connected to at least one of said enclosure assembly and said absorbent member, said means for assisting including a retention member connected to at least one of said anterior end of said absorbent member and an anterior end of said enclosure assembly.

8. A body cavity pack, as claimed in claim 1, further including:

radiopaque means for locating at least portions of one of said absorbent member and said enclosure assembly.

9. A body cavity pack, as claimed in claim 8, wherein:

said radiopaque means includes a marker element associated with at least one of said absorbent member and said enclosure assembly.

10. A medical device for absorbing body fluid, comprising:

an absorbent member for absorbing body fluid and including upper and lower sections, and anterior end and a posterior end, and first and second sides, said absorbent member having an unabsorbed state before absorbing body fluid and an absorbed state after absorbing body fluid;

a first loosely fitting bag surrounding said absorbent member and being immediately adjacent thereto, said first bag having a first set of apertures through which body fluid is able to pass to said absorbent member, said first bag except for said first set of apertures being substantially liquid impervious; and a second loosely fitting, bag surrounding said first bag, said second bag having a second set of apertures through which body fluid is able to pass to said first set of apertures, said second bag except for said second set of apertures being substantially liquid impervious;

wherein at least said first bag has an inner size and, when said absorbent member changes from said unabsorbed state to said absorbed state, said absorbent member increases in size differently from any change in size of said inner size of said first bag.

11. A medical device, as claimed in claim 10, wherein:

said second set of apertures is offset from said first set of apertures wherein body fluid passing through said second set of apertures contacts portions of said first bag in reaching said first set of apertures.

12. A medical device, as claimed in claim 10, wherein:

each of said upper and lower sections, said anterior and posterior ends, and said first and second sides has an outer surface and in which all portions of said outer surfaces are in contact with at least one of said first and second bags.

13. A medical device, as claimed in claim 10, further including:

means for assisting removal of said absorbent member and said first and second bags from a body cavity.

14. A medical device, as claimed in claim 10, further including:

radiopaque means for locating at least portions of one of said absorbent member and said first and second bags.

15. A medical device, as claimed in claim 10, wherein:

said second bag has an inner size and in which each of said inner sizes of said first and second bags remain substantially the same when said absorbent member is in said absorbed state.

16. A medical device, as claimed in claim 10, wherein:

said unabsorbed state of said absorbent member includes said absorbent member being compressed.

* * * * *